United States Patent
Song

(10) Patent No.: US 7,683,615 B2
(45) Date of Patent: Mar. 23, 2010

(54) METHOD AND APPARATUS TO IMPROVE NMR SPECTRAL RESOLUTION IN AN INHOMOGENEOUS MAGNETIC FIELD

(75) Inventor: Yi-Qiao Song, Ridgefield, CT (US)

(73) Assignee: Schlumberger Technology Corporation, Cambridge, MA (US)

( * ) Notice: Subject to any disclaimer, the term of this patent is extended or adjusted under 35 U.S.C. 154(b) by 204 days.

(21) Appl. No.: 11/613,592

(22) Filed: Dec. 20, 2006

(65) Prior Publication Data

US 2008/0150525 A1    Jun. 26, 2008

(51) Int. Cl.
*G01V 3/00*    (2006.01)
(52) U.S. Cl. .................................. 324/309; 324/307
(58) Field of Classification Search ......... 324/300–322; 600/407–435
See application file for complete search history.

(56) References Cited

U.S. PATENT DOCUMENTS

| | | | |
|---|---|---|---|
| 6,111,409 A | 8/2000 | Edwards et al. | |
| 6,346,813 B1 | 2/2002 | Kleinberg | |
| 7,053,611 B2 * | 5/2006 | Freedman | 324/303 |
| 2005/0007111 A1 * | 1/2005 | Frydman | 324/307 |
| 2008/0240530 A1 * | 10/2008 | Reese et al. | 382/131 |

OTHER PUBLICATIONS

De Graaf Robin A., "In Vivo NMR Spectroscopy, Principles and Techniques", Chapter 6, "Spectroscopic Imaging and Multi-voxel Localization", pp. 303-334, John Wiley & Sons, 1998.

* cited by examiner

*Primary Examiner*—Brij B Shrivastav
(74) *Attorney, Agent, or Firm*—James M. McAleenan; Brigid M. Laffey; Helene Raybaud

(57) ABSTRACT

A method and apparatus for improving spectral resolution of an NMR measurement in the presence of an inhomogeneous magnetic field. According to one embodiment, a method producing a high resolution nuclear magnetic resonance (NMR) spectrum for a sample in an inhomogeneous magnetic field may comprise generating a first magnetic pulse and a second magnetic pulse, the first and second magnetic pulses being separated in time by a first time period, during the first time period, generating a gradient pulse, repeating the steps of generating the first and second magnetic pulses and generating the gradient pulse N times for different values of a field strength of the gradient pulse, wherein N is an integer greater than one, after each second magnetic pulse, acquiring a signal from the sample, and producing a reconstructed high resolution NMR spectrum from the acquired signals.

19 Claims, 7 Drawing Sheets

METHOD AND APPARATUS TO IMPROVE NMR SPECTRAL RESOLUTION IN AN INHOMOGENEOUS MAGNETIC FIELD

BACKGROUND

1. Field of the Invention

The present invention relates to nuclear magnetic resonance measurements and, more particularly, to methods of improving spectral resolution in the presence of inhomogeneous magnetic fields.

2. Discussion of Related Art

Nuclear magnetic resonance (NMR) spectroscopy is one of the most used methods for the characterization of molecular species, functional groups and structures. The techniques of NMR spectroscopy are well documented in the literature. In general, an NMR apparatus may include an array of permanent magnets that produce a static magnetic field, conventionally called $B_0$, and an NMR antenna (usually including radio frequency (RF) coils) capable of generating an oscillating magnetic field, conventionally called $B_1$. The static $B_0$ and oscillating $B_1$ fields should be substantially perpendicular to one another. The $B_1$ antenna should be capable of transmitting and receiving signals at the Lamor frequency, $f_L$, given by the equation:

$$f_L = \left(\frac{\gamma}{2\pi}\right) B_0 \quad (1)$$

where $\gamma$ is the gyromagnetic ratio of the nuclear species of interest and $B_0$ is the strength of the static magnetic field. Quantitative NMR measurements may require that the nuclear spins be fully polarized by the static magnetic field prior to data acquisition. The longer the exposure to the static field before the measurement begins, the more complete the alignments of the nuclear moments (spins) by the static field. In general, for the spins to be fully polarized, the exposure time may be approximately three to five times the longitudinal relaxation time $T_1$ of the spins.

Various NMR measurements can be used to distinguish one chemical compound from another. NMR chemical shift is one such measurement. The NMR chemical shift depends on the molecular environment of a spin and is a sensitive function of the electronic structure of molecules. Thus, based on measured chemical shift, chemical conformation may be determined. Crude oil, for example, is a complex mixture of hydrocarbons and NMR spectroscopy may be used to identify hydrocarbon components as well as to distinguish the presence of hydrocarbons from the presence of water. For example, the chemical shift of protons in water is about 4 ppm (parts-per-million), about 1 ppm for aliphatic protons, and about 6-7 ppm for aromatic protons.

The resolution of an NMR spectrum is determined primarily by the inhomogeneity of the external magnetic field. In some existing well-logging tools that include NMR apparatus, such as Schlumberger's Combinable Magnetic Resonance tool (CMR™) and the MRScanner™, the magnetic field may vary by such a degree that the spectral bandwidth is limited by the excitation bandwidth. In other tools, such as the MRILab for the Reservoir Description tool from Haliburton Energy Services, the field inhomogeneity is still likely to be several ppm, or even more than tens of ppm, due to the limited precision in magnet design and construction. Even a very good magnet may have a non-uniformity of about 1%. Such resolution may be insufficient to distinguish between the chemical shifts of water and aliphatic and/or aromatic compounds which differ by only a few ppm.

SUMMARY OF INVENTION

To produce magnet assemblies capable of producing highly uniform (homogeneous) magnetic fields is often very expensive and sometimes not possible for certain applications. Therefore, it would be of considerable usefulness to improve the spectral resolution of NMR measurements under the current hardware limitations, namely without needing to improve the homogeneity of the magnetic field and thus without having to improve the magnet design. Such improved spectral resolution may allow a direct measurement of the chemical shift of fluids, for example, of water and of hydrocarbons. Accordingly, various aspects and embodiments of the invention are directed to a method of improving NMR spectral resolution an inhomogeneous magnetic field According to one embodiment, a method and apparatus for producing a high resolution nuclear magnetic resonance (NMR) spectrum for a sample in an inhomogeneous magnetic field may comprise generating a first magnetic pulse and a second magnetic pulse, the first and second magnetic pulses being separated in time by a first time period, during the first time period, generating a gradient pulse, repeating the steps of generating the first and second magnetic pulses and generating the gradient pulse N times for different values of a field strength of the gradient pulse, wherein N is an integer greater than one, after each second magnetic pulse, acquiring a signal from the sample, and producing a reconstructed high resolution NMR spectrum from the acquired signals.

In one example of such a method, producing the reconstructed high resolution NMR spectrum may include producing a two-dimensional spectrum, wherein the first dimension is spatial position in the sample and wherein the second dimension is frequency. In another example, producing the reconstructed high resolution NMR spectrum may further include determining a spatial dependence of the inhomogeneous magnetic field from the two-dimensional spectrum. In another example, producing the reconstructed high resolution NMR spectrum may further include producing a plurality of spectra, each spectrum of the plurality of spectra corresponding to an acquired signal, shifting in frequency the plurality of spectra based on the determined spatial dependence of the inhomogeneous magnetic field, and summing the plurality of spectra to obtain the reconstructed high resolution NMR spectrum. The plurality of spectra may be produced by performing a Fourier transform on each of the acquired signals. In one example, each successive gradient pulse may have a field strength that differs from the preceding gradient pulse field strength by an amount equal to a gradient step size. In another example, generating the gradient pulse may include applying the gradient pulse to the sample along a direction of greatest inhomogeneity of the inhomogeneous magnetic field.

BRIEF DESCRIPTION OF THE DRAWINGS

Various aspects and embodiments of the invention are described below with reference to the accompanying figures. In the drawings, which are not intended to be drawn to scale, each identical or nearly identical component that is illustrated in various figures is represented by a like numeral. For purposes of clarity, not every component may be labeled in every drawing.

DETAILED DESCRIPTION

Figure 1:
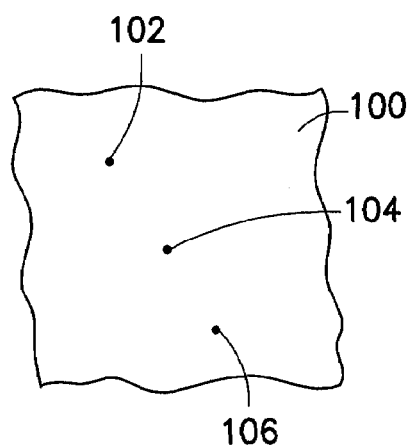
FIG. 1 is a diagram of a sample containing nuclear spins of interest.

As discussed above, nuclear magnetic resonance (NMR) chemical shift is a useful measurement that can be used to distinguish one chemical compound from another. However, the applicability of the measurement may be limited by inhomogeneities in the magnetic field. Many magnet assemblies, particularly those used in well-logging applications, comprise pre-machined, magnetized slabs and may have a field homogeneity no better than a few parts-per-million (ppm), if that, due to design and limited manufacturing precision. Even if the field homogeneity could be improved during assembly of the magnet, the magnet is unlikely to remain so well shimmed after being installed in a tool and operated in environments with varying temperatures. Therefore, aspects and embodiments of the invention are directed to a method for improving NMR spectral resolution in the presence of inhomogeneous magnetic fields. Embodiments of the method may allow for high resolution measurements under existing hardware limitations, for example, while using existing magnet assemblies that produce inhomogeneous fields. In particular, according to some embodiments, magnetic field gradient pulses may be used to improve the spectral resolution, as discussed further below.

It is to be appreciated that this invention is not limited in its application to the details of construction and the arrangement of components set forth in the following description or illustrated in the drawings. The invention is capable of other embodiments and of being practiced or of being carried out in various ways. For example, it is to be appreciated that the method apparatus described herein is not limited to use in wellbores and may be used in a variety of environments and applications. Examples of specific implementations are provided herein for illustrative purposes only and are not intended to be limiting. In particular, acts, elements and features discussed in connection with one embodiment are not intended to be excluded from a similar role in other embodiments. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Figure 2:
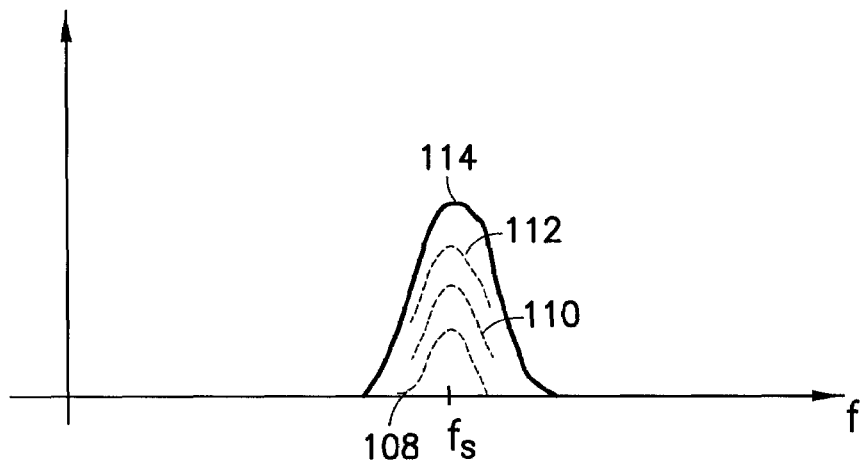
FIG. 2 is an illustrative plot of an NMR spectrum versus frequency from spins in a homogeneous field.
Figure 3:
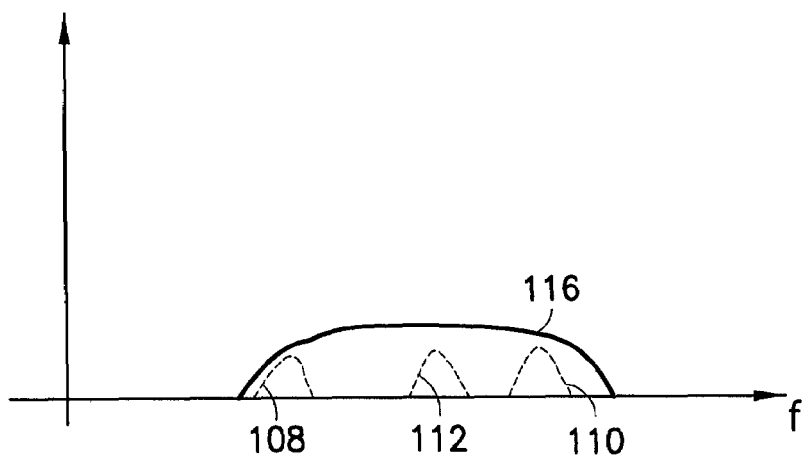
FIG. 3 is another illustrative plot of an NMR spectrum versus frequency from spins in an inhomogeneous field.

NMR measurements are volumetric averages, wherein the many nuclei in a sample all contribute to a combined detected signal. Referring to FIG. 1, there is illustrated a diagram of a sample 100 include three representative nuclei 102, 104, 106 (of the same species) arbitrarily located in the sample. If the magnetic field across the sample were homogeneous, all of the nuclei (of a given species) would give a signal at the same frequency. This scenario is illustrated in FIG. 2 which shows an illustrative plot of signal strength versus frequency (on the horizontal axis). In a homogeneous field, the signal from each individual nucleus (e.g., signal 108 from nucleus 102, signal 110 from nucleus 104 and signal 112 from nucleus 106) is at approximately the same frequency, $f_L$. Thus, the combined signal 114, a sum of all of the individual signals, provides a relatively sharp peak at the Lamor frequency of the nuclei of interest. By contrast, when the sample is in an inhomogeneous field, the signal from the different nuclei in the sample may appear at different frequencies due to the gradients in the magnetic field. This scenario is illustrated in FIG. 3. In the presence of an inhomogeneous field, the signals 108, 110, 112 from individual nuclei and are different frequencies and thus the combined signal 116 provides a broad, lower amplitude peak.

As used herein, the term "broad line signal" or "broad line spectrum" refers to an NMR signal obtained from a sample in an inhomogeneous magnetic field and which is thus broadened by the field inhomogeneity, for example, signal 116 in FIG. 3. The term "high resolution signal" or "high resolution spectrum" refers to the theoretical NMR signal that would be recovered from such a sample were the magnetic field substantially homogeneous, for example, signal 114 in FIG. 2. Mathematically, the broad line spectrum $S(\omega)$, is an integral of the intrinsic signal over the sample volume, given by the following equation:

$$S(\omega) = \int dv \cdot s(\omega') \delta(\omega' - f(r)) \qquad (2)$$

where $s(\omega)$ is the high resolution signal and the function $f(r)$ describes the frequency offset at position r that results from the field inhomogeneity. The function $\delta(\ )$ is the delta function defined as: $\delta(x)=0$ for $x \neq 0$ and $\int dx \delta(x) = 1$.

Figure 4:
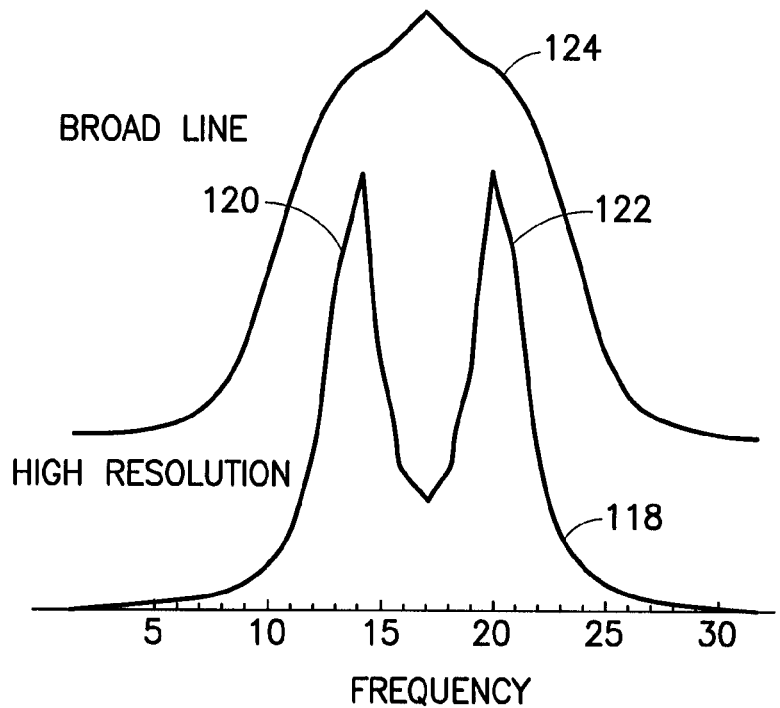
FIG. 4 is a plot of a broad line spectrum and an high resolution spectrum as a function of frequency.

When the magnetic field is well shimmed, $f(r)=0$ and the intrinsic or high resolution spectrum $s(\omega) \equiv S(\omega)$. This corresponds to the case illustrated in FIG. 2. However, when the range of the function $f(r)$ is large compared to the spectral features of $s(\omega)$, it may become difficult to reconstruct $s(\omega)$ from a measured broad line spectrum $S(\omega)$. The magnetic field inhomogeneity broadens the NMR spectrum, as can be seen in FIG. 3, and degrades the resolution of the measurement. As a result, it may not be possible to distinguish signals from different nuclei at slightly different frequencies because individual resonance peaks may be lost within the broadened peak that arises due to the inhomogeneities in the magnetic field. This is illustrated in FIG. 4 which shows a signal plot versus frequency. A high resolution signal 118 includes two peaks 120, 122 corresponding to resonance signals from two different types of nuclei, e.g., water and a hydrocarbon. However, in the spectrum 124 (corresponding to a measurement of $S(\omega)$) that is broadened by field inhomogeneity, these two resonance peaks cannot be distinguished.

According to one embodiment, there is provided a method and apparatus to allow recovery of different resonance peaks, for example, closely spaced chemical shifts of different molecules, from a broad line measurement. In one embodiment, this method is based on the realization that although field inhomogeneity appears in the spin Hamiltonian in a very similar way to the chemical shift, the spatial dependence distinguishes them. The magnetic field inhomogeneity is the difference in field strength at different positions in space, particular, at different spatial positions in a sample. Therefore, if the NMR spectrum were to be acquired from a very small volume of the sample, the field inhomogeneity would be reduced. However, direct application of this principle, using a very small NMR coil, reduces the signal strength because far fewer nuclei are present in the small volume and thus there are fewer contributions to the overall detected signal. As a result, difficulties may arise in that the signal to noise ratio may be reduced such that accurate detection is no longer possible.

According to one embodiment, magnetic field gradients may be used to improve the spectral resolution without the above-mentioned loss of signal intensity. Phase encoding measurements, using magnetic field gradient pulses, may be used to determine the full spatial dependence of the magnetic field, f(r). As discussed below, the gradient pulses in a given dimension act to select a "slice" of the sample in that dimension, corresponding to a small volume within which the field may be substantially homogeneous, or at least the field inhomogeneity may be substantially reduced. A series of gradient pulses may be used to sequentially select different slices and to thereby determine at least an estimate of the spatial dependence of the magnetic field, f(r). The spectra of all the slices may then be frequency-corrected according to the now-known (or estimated) f(r) and summed to provide a reconstructed high resolution signal. The signal-to-noise ratio may be maintained by the summing of all the slices, thereby overcoming the above-mentioned problem of the signal strength being small for individual slices. This method may be robust even if the spatial dependence of the magnetic field is complex. The technique is referred to herein as spatially resolved spectroscopy because the phase encoding measurements are used to resolve or determine the spatial dependence f(r) and therefore, allow a high resolution signal to be reconstructed.

Figure 5:
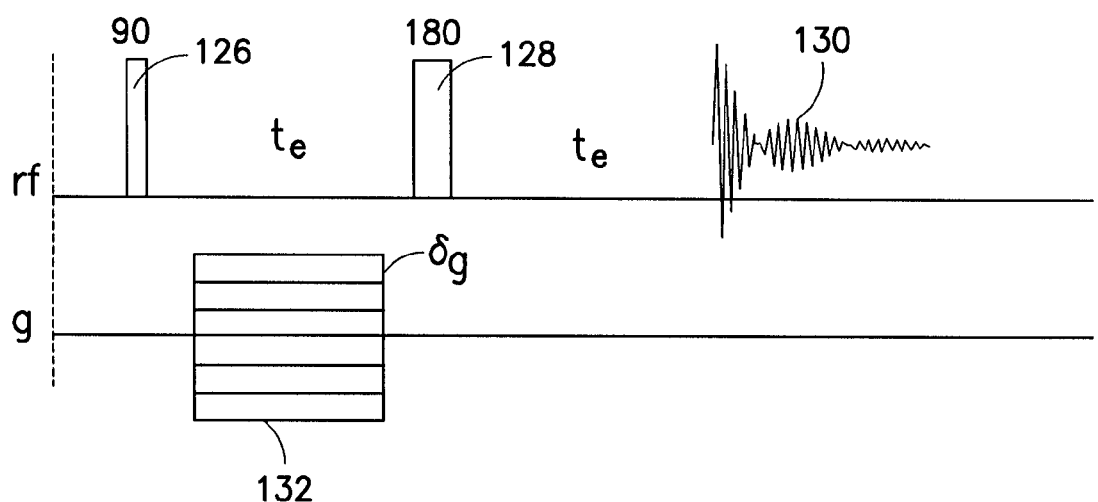
FIG. 5 is a pulse diagram of one example of a pulse sequence that may be used for spatially resolved NMR spectroscopy according to an embodiment of the invention.

Referring to FIG. 5, there is illustrated one example of a pulse sequence that may be used to acquire such spatially resolved spectra. A main goal of this pulse sequence is to separate the spatial field variation from the chemical shift. The pulse sequence includes a radio frequency (RF) sequence and a series of magnetic field gradient pulses. The radio RF pulse sequence is a spin-echo sequence containing a 90 degree pulse 126 and a 180 degree pulse 128 spaced apart from the 90 degree pulse 126 by a time spacing $t_e$. The initial 90 degree RF pulse 126 may be applied to disturb the equilibrium magnetization of the spins. Next, the 180 degree RF pulse 128, called the π pulse, may be applied to refocus the de-phasing of the spins. The time $t_e$ may be referred to as the echo spacing. A spin echo signal 130 may be acquired a time period $t_e$ after the 180 degree pulse 128.

According to one embodiment, the gradient pulses 132 may be applied to the sample between the 90 degree and 180 degree pulses, as shown in FIG. 5. In one example, one gradient pulse may be applied for each pair of 90 and 180 degree pulses. In other words, after the 90 pulse 126 is generated, a gradient pulse may be generated, followed by the 180 degree pulse 128. The steps may be repeated N times, for different field strength values of the gradient pulse. In one example, the gradient strength may be varied from $-\delta gN/2$ to $+\delta gN/2$, where $\delta g$ is the step of the gradient strength and N is total the number of gradient steps or acquisitions. It is to be appreciated that the gradient strength variation is not limited to being symmetrical, but may instead be varied, for example, from $\delta g$ to $\delta gN$, or over some other range that includes some negative strengths and some positive strengths. For each gradient value, a signal 130 may be acquired.

For the most general case, the magnetic field may vary in all three spatial dimensions, x, y, z and thus f(r) may be f(x,y,z). The broad line signal may be described mathematically in the time domain according to the following equation:

$$S(t)=\int s(t)\exp(i[f(x,y,z)t+\omega t])dxdydz \quad (3)$$

where:
s(t) is the time domain free induction decay signal;
f(x,y,z) is the spatial variation of the magnetic field; and
ωt is the natural frequency.

Accordingly, gradient pulses may be applied in along all three x, y, z axes in the volume sample. The signal from equation (3) may therefore be rewritten:

$$S(t,k)=\int s(t)\exp(ik_x x+ik_y y+ik_z z)\exp(i[f(x,y,z)t+\omega t])dxdydz \quad (4)$$

where $k_x=\gamma g_x \tau$, $k_y=\gamma g_y \tau$, $k_z=\gamma g_z \tau$, and $g_x$, $g_y$ and $g_z$ are the gradients along x, y, and z direction, respectively. τ is the time duration of the gradient pulse. A series of gradient pulses may be applied along each dimension, stepping with a given gradient step size over a range of strengths along each axis, as discussed above.

According to one embodiment, a two-dimensional Fourier transform may be applied to the data described by equation (4). The stepping of the gradient is defined to be the first dimension. This is a positional dimension, each gradient corresponding to a small slice of the sample in the direction in which the gradient is applied. Frequency is the second dimension. To illustrate this principle, for simplicity, the magnetic may be assumed to be varying in only one direction, for example, the z direction. Gradient pulses can therefore be applied in the z direction, using for example, the pulse sequence illustrated in FIG. 5. In this case, equation (4) may be rewritten:

$$S(t,k)=\int s(t)\exp(ikz)\exp(i[f(z)t+\omega t])dz \quad (5)$$

If a Fourier transform of equation (5) is taken with respect to k, the result is given by the following equation:

$$\overline{S}(t,z)=\int s(t)\exp(i[f(z)t+\omega t])dz \quad (6)$$

Figure 6:
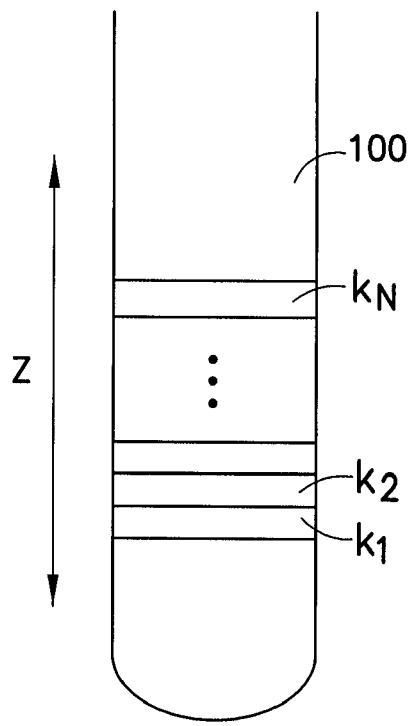
FIG. 6 is a diagram of a sample showing slices in the z-direction corresponding to different gradients k.

The signal given by equation (6) is equivalent to a measured signal in a very small volume at one position in z in the sample. Thus, the method of gradient stepping and acquiring a signal for each step and the subsequent Fourier transformation may be equivalent to dividing the sample into multiple very small slices of the sample volume, which as discussed above, reduces the field inhomogeneity. This is illustrated, for example, in FIG. 6, where gradients $k_1$ to $k_N$ along the z direction effectively slice the sample 100 along the z direction. In this manner, the gradient pulses provide phase encoding of the spatial dimension.

Figure 7:
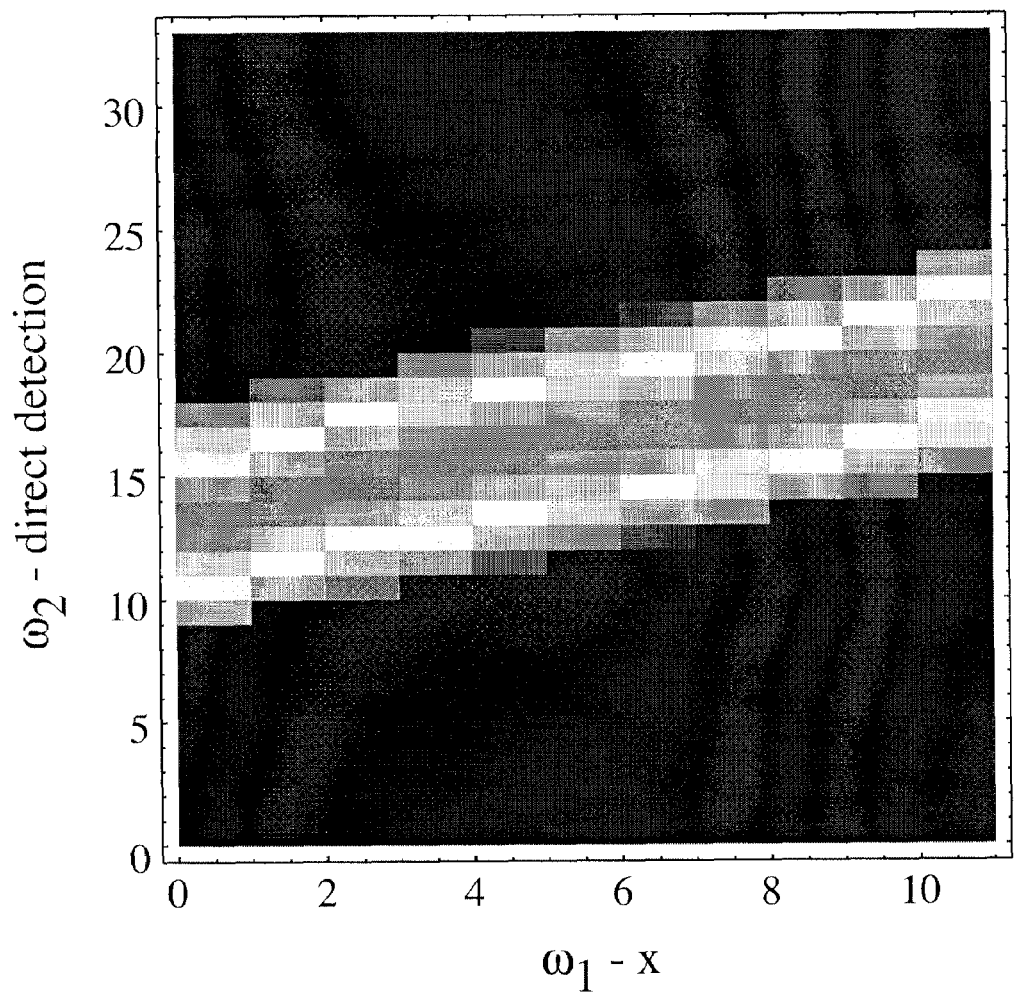
FIG. 7 is a spatially resolved two dimensional NMR spectrum.

The resolution in the first dimension is determined by the gradient step size δg and the total number of steps N to be 1/δgN with the unit of length. A first order phase correction, as understood by one skilled in the art, may be applied along the first dimension and the imaginary part of the data should vanish due to symmetric sampling. The second dimension is frequency. Thus, acquired signal after each gradient step produces a signal at a certain frequency and spatial information is given by the gradient. Phase correction may also be applied to the second dimension as understood by one skilled in the art. The result is then the spectrum along $\omega_2$ (frequency) as a function of position ($\omega_1$). Referring to FIG. 7, there is illustrated an example of such a spatially resolved two-dimensional spectrum, corresponding to the signals of FIG. 4. It can be seen that the two resonance lines 120 and 122 are visible, appearing as two different frequencies at the same position, in the spatially resolved two-dimensional spectrum. One skilled in the art will readily recognize that the output depicted graphically in FIG. 4 is only one example of the use of the high resolution NMR spectra of the present application.

As discussed above, once the spatial dependence of the magnetic field is known, the measured spectra for each slice may be shifted according to f(r) (providing frequency correction) and summed to produce an overall signal. A function describing f(r) can be determined in numerous ways from the two-dimensional position-frequency ($\omega_1$-$\omega_2$) spectrum. For example, a fitting of f(r) may be performed. One example of such a fitting technique may be to perform a fitting of f(r) to maximize the following function:

$$\chi = \left[ \sum_{\omega} \sum_{i=-N/2}^{i=N/2-1} S(x=i, \omega - f(i)) \right]^2 \quad (7)$$

The resulting f(i) may then be used to shift the spectra of each slice and the final recovered high resolution spectrum may be given by:

$$s(\omega) = \sum_{i=-N/2}^{i=N/2-1} S(x=i, \omega - f(i)) \quad (8)$$

Using an appropriate gradient step size and number of gradient steps, there may be no significant signal-to-noise penalty. However, if very small step size, and/or many gradient steps are needed to compensate for large field variation, a longer time may be needed to perform the entire acquisition. It is to be appreciated that the invention is not limited to the use of the fitting function described in equation (7) and many other fitting functions may be suitable, as would be recognized by those skilled in the art. In addition, other techniques besides fitting may also be used to determine or estimate the magnetic field variation. For example, sophisticated pattern recognition software may be useful to better determine f(r), particularly under poor signal-to-noise ratio conditions.

The above-described method is robust even if the spatial dependence of the magnetic field is complex. However, it may take many scans (many different gradient steps along multiple axes) to determine the full three-dimensional spatial dependence f(r). In some circumstances, the spatial dependence of the magnetic field may be simpler. For example, the field may be substantially inhomogeneous in only one or two spatial dimensions, rather than in all three. In addition, according to one embodiment, although there may be field variation in all three directions, it may be sufficient to apply gradient pulses along only the direction of largest field inhomogeneity. Therefore, for simplicity in the following discussion, it may be assumed that the magnetic field varies only in the z dimension. However, it is to be appreciated that the following applies equally to field variation in other dimensions and also to field variation in multiple dimensions, although in that case, the mathematics is more complex. For example, it can be assumed that f(r)=Az, where z is a spatial coordinate and A is a constant characterizing the corresponding field gradient in the z direction. In this case, the time domain signal is given by:

$$S(t,k) = \int_{-a}^{a} s(t) e^{iAzt} e^{+ikz} = s(t) \frac{\sin(At+k)a}{At+k} \quad (9)$$

where 2a is the length of the sample in the z direction. Since A and s(t) are the only unknowns, two sets of measurements with different k (different gradient strengths) may uniquely determine A and s(t) for all t. A Fourier transform of s(t) may provide the high resolution spectrum.

It will be appreciated by those skilled in the art, that this simplified method may only work when (At+kδ) is relatively small, due to the decaying function form of:

$$\frac{\sin(At+k)a}{At+k} \quad (10)$$

In a unique case when A and k are of opposite sign, then (At+k) will cross zero at some value of t. At this value of t, the following condition is satisfied:

$$\frac{\sin(At+k)a}{At+k} = 1 \quad (11)$$

and the signal may be maximized in a form of echo. At the t values around this echo, the value of (11) is close to unity and A may be obtained accurately. As a result, several measurements with different gradients k may be needed to recover the high resolution spectrum.

It is further to be appreciated that the functional form of f(r) may be more complex that a constant gradient in one direction. For example, f(r) may vary in the x direction and have the form:

$$f(r)=Ax+Bx^2 \quad (12)$$

where A and B are constants characterizing the field gradient. The above described technique may be used to determine these gradient parameters (A and B) by performing several measurements with different gradients, for example a different k. Furthermore, as discussed above, the field dependence f(r) may exhibit constant, or non-constant gradients in more than one dimension. In this case, as discussed above, several measurements may be performed using a combination of gradient pulses along different directions so as to obtain at least an estimate of the full spatial dependence of the magnetic field. In these more complex situations, fitting of f(r) or pattern recognition techniques may be needed or preferred to determine f(r) from the results of the series of measurements.

Figure 8:
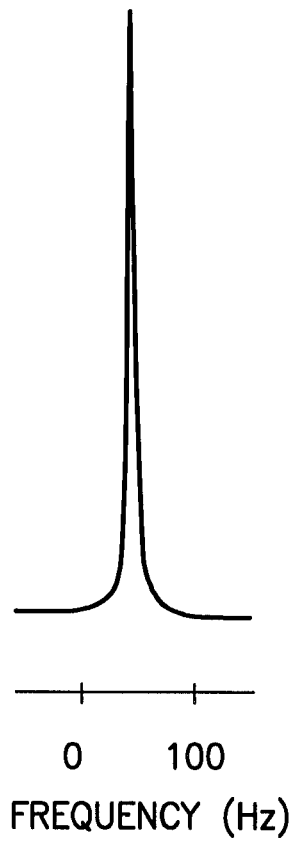
FIG. 8 is a high resolution spectrum from a water sample using a well shimmed magnet.

An example was done using the pulse sequence of FIG. 5 to perform spatially resolved spectroscopy on a sample of water. The water sample was cylindrical, 2 inches long and 0.35 inches in diameter (contained in a tube). In a first measurement, the magnet was well shimmed to produce a high resolution signal, illustrated in FIG. 8. The intrinsic linewidth of the water sample is very narrow (a few Hz) as visible as the resonance peak at a frequency of about 50 Hertz (Hz). The magnet shim was then intentionally adjusted to produce a varying magnetic field in the z direction, resulting in a broad line shape for a direct NMR measurement. Referring to FIG.

9, the broad line NMR spectrum is illustrated over a frequency range of −1000 Hz to 1000 Hz. The spectrum, broadened by the magnetic field inhomogeneity in the z direction obscures the peak of the water sample and thus the chemical shift of the water sample. Next, a series of measurements were conducted in which the pulse sequence of FIG. 5 was applied to the sample using 64 gradient steps.

Figure 9:
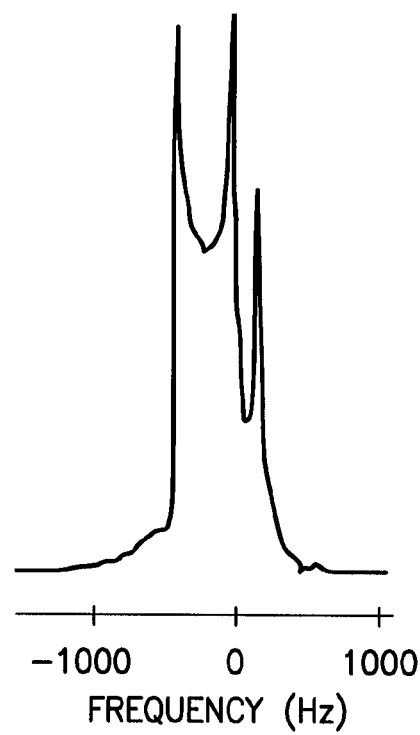
FIG. 9 is a broad line spectrum from the same water sample.
Figure 10:
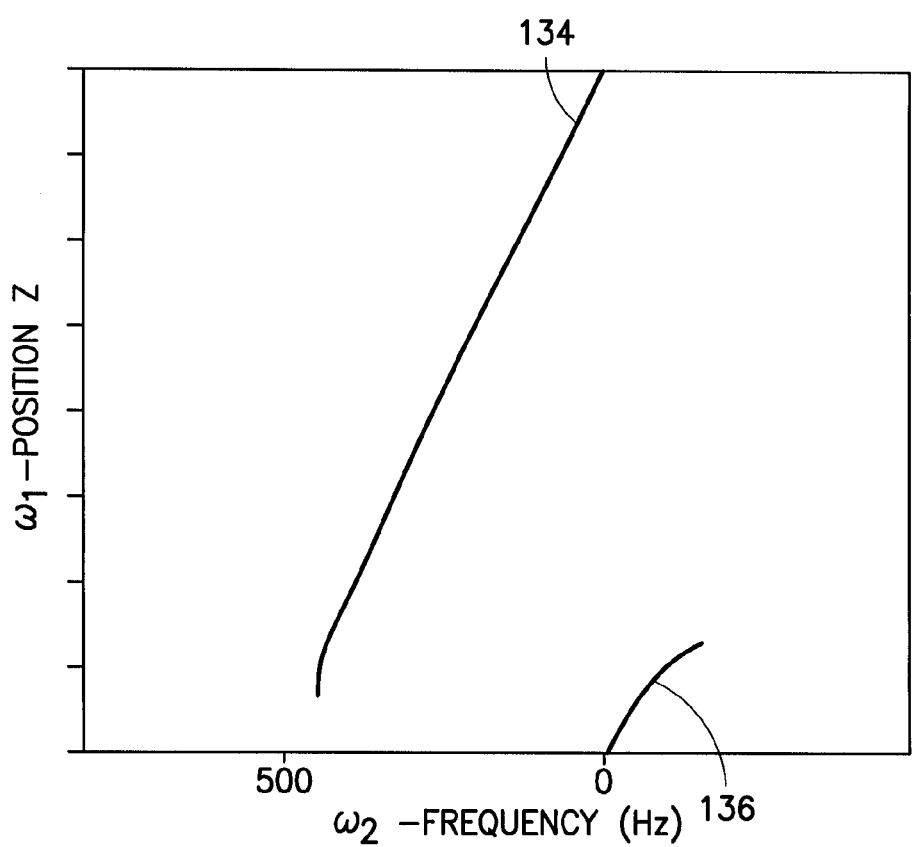
FIG. 10 is a spatially resolved two dimensional spectrum from the same water sample, according to an embodiment of the invention.
Figure 11:
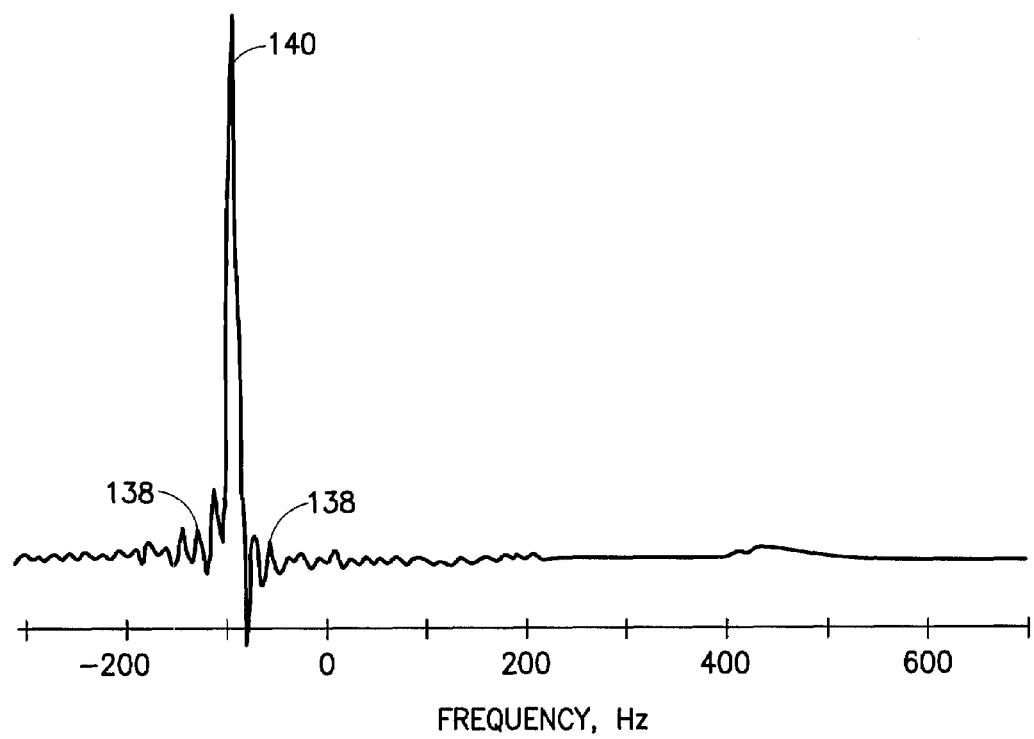
FIG. 11 is a reconstructed spectrum from the same water sample, according to an embodiment of the invention.

Referring to FIG. 10, there is illustrated a resulting two dimensional spatially resolved spectrum for this example. The spectrum shows a narrow resonance line 134 at different frequencies ($\omega_2$) at each slice position (from each gradient step) along $\omega_1$ (the spatial dimension defined by the stepping of the gradient). It can be seen that the positional dependence of the frequency of the resonance lines appears to be linear. This is consistent with the set-up of the example, in which the magnet was intentionally adjusted to have inhomogeneity along one dimension (the z dimension). The foldover 136 along $\omega_2$ is due to the value of the gradient step. An estimate of f(r) was assumed to be a linear gradient along the z dimension, in accordance with FIG. 10, and the two dimensional spectrum was corrected by shifting the spectrum to align the peak of each slice in frequency. The summation of all the shifted spectra produces the corrected high resolution spectrum illustrated in FIG. 11. The "bumps" 138 around the peak 140 in the corrected spectrum are due to truncations. As can be seen by comparing FIGS. 9 and 11, the reconstructed spectrum (FIG. 11) produced using spatially resolved spectroscopy according to the invention is very similar to the high resolution spectrum measured with a very well shimmed magnet. This example therefore, shows that the method may allow chemical shift measurements in inhomogeneous magnetic fields.

Spatially resolved spectroscopy according to embodiments of the invention may be implemented in a variety of ways and applied to various measurements including, but not limited to, chemical shift. For example, various in vivo NMR spectroscopy methods used in medicine may be applicable to the chemical shift analysis discussed herein (see, for example, R. A. de Graaf, *In vivo NMR Spectroscopy*, John Wiley and Sons, Baffins Lane, Chichester, West Sussex PO19 1UD. England, 2002).

According to one embodiment, a method of spatially resolved NMR spectroscopy may include phase encoding for spatial dimensions, as discussed above. The combination of the use of gradient pulses and the mathematical analysis may be used to effectively slice a sample into small volumes in each dimension in which the gradients are applied. Mathematical analysis, such as the Fourier transforms discussed above, may be used to obtain the spectrum for each slice, corresponding to each gradient pulse, as discussed above. Chemical shift modulation of the spectrum may then be directly obtained in the time domain using a pulse sequence such as that illustrated in FIG. 4. In another embodiment, a gradient echo train may be used, similar to techniques of echo planar imaging (EPI) known to those skilled in the art. As understood by one skilled in the art, the EPI method uses a train of gradient pulses containing alternating gradient pulses along one dimension and other gradient pulses along other dimensions to achieve spatial imaging while maintaining the chemical shift evolution. The gradient echo train method may be faster than other methods because only a single acquisition may be needed to obtain the multi-dimensional spectrum.

Figure 12:
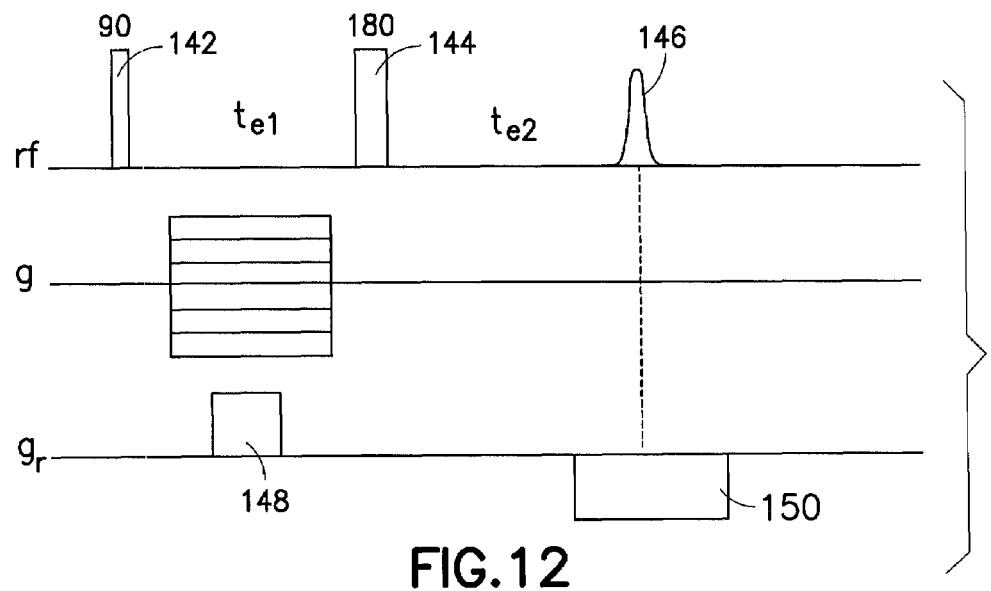
FIG. 12 is a pulse diagram of another example of a pulse sequence that may be used for spatially resolved NMR spectroscopy, according to an embodiment of the invention.

According to another embodiment, both phase and frequency encoding may be used for the spatial dimensions. As seen in FIG. 12, the gradient pulse 132 of FIG. 5 is called phase encoding because it is applied not during signal acquisition. Freq encode is gradient during signal acquisition, such as the combination of 148 and 150 in FIG. 12. 148 and 150 are called the read gradient because it is on during reading or acquisition. The chemical shift modulation may then be obtained in an indirect dimension as described below. One example of a pulse sequence that may be used for this embodiment is illustrated in FIG. 12. An RF spin-echo pulse sequence including a 90 degree pulse 142 and a 180 degree pulse 144 may be used for the spatially resolved spectroscopy. Signals 146 may be acquired at a time $t_{e2}$ after the 180 degree pulse 144. The time between the 90 degree pulse and the 180 degree pulse, $t_{e1}$, may be fixed for an entire measurement (which may include multiple acquisitions of the signal 146). The read gradient 148 and 150 may be set such that an echo 146 appears centered at the time $t_{e2}$ after the 180 degree pulse. The times $t_{e1}$ and $t_{e2}$ may be the same or different. The read gradient 150 may be used for a variety of purposes. For example, the read gradient 150 may be used to do imaging along the read-grad direction. Additionally, the read gradient 150 may be used, in combination with 148, is to shift the echo position. For example, the amplitude of 148 and 150 is often set to be the same and 150 is twice as long as 148. Then the echo will occur in the middle, i.e. te1=te2. By having different amplitudes of 148 and 150, the echo can occur away from the center so that te1−te2 is non-zero. This is one suitable way to measure the chemical shift effect wherein the time te1−te2 is the so-called chemical shift evolution. The phase encoding gradient pulses may be applied during time $t_{e1}$, as discussed above. The chemical shift modulation may be obtained by performing several measurements with different $t_{e2}$. The chemical shift evolution time may be given by $t_{e2}-t_{e1}$. The read gradient 148 and 150 and other phase encoding gradient pulses are used for the spatial dimensions of the sample.

The principles of spatially resolved NMR spectroscopy according to embodiments of the invention may be applied to an arbitrary magnetic field distribution. Thus, the methods may be used to obtain reconstructed high resolution spectra, and thus, for example, chemical shift measurements, without requiring any improvement the homogeneity of fields produced by existing magnet assemblies that are used, for example, in well-logging and other applications. However, if the magnetic field is inhomogeneous in all three spatial directions, x, y, z, and gradients are applied along all three directions, the entire signal acquisition may take a long time; too long for some applications. For example, in a down-hole environment, the available acquisition time may be limited by logging speed and/or by the uniformity of the sampled formation fluid because the tool and/or the sample may be moving. Therefore, techniques may be used to speed up the measurement, while retaining sufficient accuracy. For example, according to one embodiment discussed above, gradient pulses may be applied along the strongest field gradient direction, rather than along all three directions. The suitable application of gradient pulses along less than all three directions is influenced by a variety of factors. For example, the size and strength of the other gradients are and what resolution is required for a particular application may influence the application of gradient pulses. In one example, if the other gradients (times the sample sizes in those dimensions) only produce broadenings smaller when compared to the spectral features to be resolved, then these gradients do not need to be corrected. In the alternative, if these gradients produce large broadenings when compared to the spectral features to be resolved, these gradients may require correction. When the signal-to-noise ratio is favorable, the waiting time between acquisitions may be reduced, allowing for a faster measurement time. In another example, the gradient step size and gradient field strength may be selected to allow a certain level of foldover along the first dimension in order to speed up the measurement by performing fewer phase-encoding gradient values.

Figure 13:
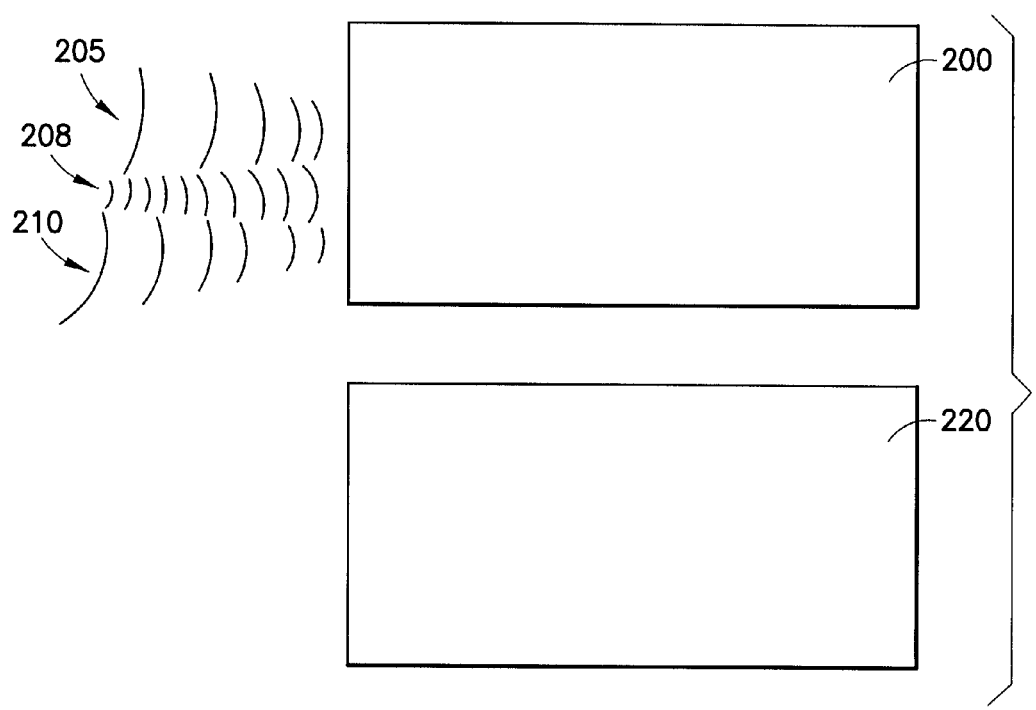
FIG. 13 is an illustrative embodiment of an apparatus for practicing the present invention.

As discussed above, the present invention may be practiced using a suitable apparatus for producing a high resolution nuclear magnetic resonance spectrum for a sample in an inhomogeneous magnetic field. One such apparatus is illustrated in FIG. 13, which includes a magnetic pulse generator 200 and a signal acquisition element 220. The magnetic pulse generator is capable of generating a first magnetic pulse 205 and a second magnetic pulse 210 wherein the first magnetic pulse 205 and the second magnetic pulse 210 are separated in time by a first time period (not shown) during which a gradient pulse 208 is generated. In one embodiment, the NMR apparatus may include an array of permanent magnets that produce a static magnetic field, $B_0$, and an NMR antenna including RF coils capable of generating an oscillating magnetic field, $B_1$. The $B_1$ antenna should be capable of transmitting and receiving signals at the Lamor frequency of nuclei of interest. An example of a down-hole tool that includes an NMR apparatus is described in U.S. Pat. No. 6,346,813 to Kleinberg, which is herein incorporated by reference. To implement the methods of embodiments of the invention on such or a similar an NMR apparatus, a pulse gradient module may be included in the tool. The pulse gradient module includes gradient coils, for example, a pair of saddle coils potted together with the RF coil that generates $B_1$, as discussed in the '813 patent referenced above. Adding a pulse gradient module to a down-hole NMR tool may add substantial complexity in mechanical engineering and electronics for power handling. However, the additional electrical power needed for the gradient pulses may in fact be modest since the gradient pulses may be applied for only a very short time interval, for example, on the order of a few milliseconds. In addition, if the two-dimensional data is to be processed on the tool, an onboard computer or processor capable of performing Fourier transforms and nonlinear fitting may be required. However, despite the added complexity of the instrumentation, the benefit of high resolution in situ measurements may provide a significant benefit and advance for fluid characterization. Furthermore, in some NMR apparatus, a gradient module may be already included to perform other pulse field gradient measurements, such as diffusion based measurements. Such apparatus may already include the equipment needed to implement spatially resolved spectroscopy according to embodiments of the invention. In another example, some down-hole NMR apparatus may include a gradient module incorporated into the magnet design and capable of providing linear gradient correction so as to maintain the uniformity of the magnetic field down-hole. Such a gradient module may be capable of allowing the spatially resolved spectroscopy discussed above to further improve spectral resolution. Thus, in some circumstances, little modification to existing equipment may be needed to employ the principles of the invention discussed herein.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. It is to be appreciated that the invention is not limited to the specific examples described herein and that the principles of the invention may be applied to a wide variety of applications and incorporated into many different embodiments. The scope of the invention should be determined from proper construction of the appended claims and their equivalents.

What is claimed is:

1. A method of producing a high resolution nuclear magnetic resonance (NMR) spectrum for a sample in an inhomogeneous magnetic field, the method comprising:
   generating a first magnetic pulse and a second magnetic pulse of the same frequency, the first and second magnetic pulses being separated in time by a first time period;
   during the first time period, generating a gradient pulse;
   repeating the steps of generating the first and second magnetic pulses and generating the gradient pulse N times for different values of a field strength of the gradient pulse, wherein N is an integer greater than one,
   after each second magnetic pulse, acquiring a signal from the sample; and
   producing a reconstructed high resolution NMR spectrum from the acquired signals.

2. The method as claimed in claim 1, wherein producing the reconstructed high resolution NMR spectrum includes producing a two-dimensional spectrum; wherein the first dimension is spatial position in the sample and wherein the second dimension is frequency.

3. The method as claimed in claim 2, wherein producing the reconstructed high resolution NMR spectrum further includes determining a spatial dependence of the inhomogeneous magnetic field from the two-dimensional spectrum.

4. The method as claimed in claim 3, wherein producing the reconstructed high resolution NMR spectrum further includes:
   producing a plurality of spectra, each spectrum of the plurality of spectra corresponding to an acquired signal;
   shifting in frequency the plurality of spectra based on the determined spatial dependence of the inhomogeneous magnetic field; and
   summing the plurality of spectra to obtain the reconstructed high resolution NMR spectrum.

5. The method as claimed in claim 4, wherein producing the plurality of spectra includes performing a Fourier transform on each of the acquired signals.

6. The method as claimed in claim 1, wherein each successive gradient pulse has a field strength that differs from the preceding gradient pulse field strength by an amount equal to a gradient step size.

7. The method as claimed in claim 1, wherein generating the gradient pulse includes applying the gradient pulse to the sample along a direction of greatest inhomogeneity of the inhomogeneous magnetic field.

8. An apparatus for producing a high resolution nuclear magnetic resonance (NMR) spectrum for a sample in an inhomogeneous magnetic field, the apparatus comprising:
   a magnetic pulse generator capable of generating a first magnetic pulse and a second magnetic pulse of the same frequency, the first and second magnetic pulses being separated in time by a first time period during which a gradient pulse is generated;
   a signal acquisition element capable of acquiring a signal from the sample after the second magnetic pulse; wherein
   the magnetic pulse generator and signal acquisition element are used to produce a reconstructed high resolution NMR spectrum from the acquired signals.

9. The apparatus of claim 8, wherein the magnetic pulse generator generates the the first and second magnetic pulses and the gradient pulse N times for different values of a field strength of the gradient pulse, wherein N is an integer greater than one.

10. The apparatus of claim 8, wherein producing the reconstructed high resolution NMR spectrum includes producing a two-dimensional spectrum; wherein the first dimension is spatial position in the sample and wherein the second dimension is frequency.

11. The apparatus of claim 10, wherein producing the reconstructed high resolution NMR spectrum further includes determining a spatial dependence of the inhomogeneous magnetic field from the two-dimensional spectrum.

12. The apparatus of claim 11, wherein producing the reconstructed high resolution NMR spectrum further includes:
   producing a plurality of spectra, each spectrum of the plurality of spectra corresponding to an acquired signal;
   shifting in frequency the plurality of spectra based on the determined spatial dependence of the inhomogeneous magnetic field; and
   summing the plurality of spectra to obtain the reconstructed high resolution NMR spectrum.

13. The apparatus of claim 12, wherein producing the plurality of spectra includes performing a Fourier transform on each of the acquired signals.

14. The apparatus of claim 9, wherein each successive gradient pulse has a field strength that differs from the preceding gradient pulse field strength by an amount equal to a gradient step size.

15. The apparatus of claim 8, wherein generating the gradient pulse includes applying the gradient pulse to the sample along a direction of greatest inhomogeneity of the inhomogeneous magnetic field.

16. The apparatus of claim 8, wherein said apparatus includes one or more permanent magnets capable of producing a static magnetic field.

17. The apparatus of claim 8, wherein said apparatus includes one or more NMR antenna, wherein said one or more antenna includes one or more RF coils capable of generating an oscillating magnetic field.

18. A means for producing a high resolution nuclear magnetic resonance (NMR) spectrum for a sample in an inhomogeneous magnetic field, comprising:
   a means for generating a first magnetic pulse and a second magnetic pulse of the same frequency, the first and second magnetic pulses being separated in time by a first time period during which a gradient pulse is generated;
   a means for acquiring a signal from the sample after the second magnetic pulse; and
   a means for producing a reconstructed high resolution NMR spectrum from the acquired signals.

19. The means for producing a high resolution nuclear magnetic resonance spectrum of claim 18, further comprising the means for repeating the steps of generating the first and second magnetic pulses and generating the gradient pulse N times for different values of a field strength of the gradient pulse, wherein N is an integer greater than one.

* * * * *